US012693668B2

(12) United States Patent
Kim et al.

(10) Patent No.: US 12,693,668 B2
(45) Date of Patent: Jul. 28, 2026

(54) DISINFECTION ROBOT AND CONTROLLING METHOD THEREOF

(71) Applicant: HDHyundai Robotics Co., Ltd., Daegu (KR)

(72) Inventors: Tae Hyun Kim, Daegu (KR); In Hwan Jung, Daegu (KR); Jong Wook Kim, Daegu (KR); Jong Kyu Oh, Daegu (KR)

(73) Assignee: HDHYUNDAI ROBOTICS CO., LTD., Daegu (KR)

( * ) Notice: Subject to any disclaimer, the term of this patent is extended or adjusted under 35 U.S.C. 154(b) by 173 days.

(21) Appl. No.: 18/374,945

(22) Filed: Sep. 29, 2023

(65) Prior Publication Data

US 2024/0118698 A1     Apr. 11, 2024

(30) Foreign Application Priority Data

Sep. 30, 2022    (KR) ........................ 10-2022-0125838

(51) Int. Cl.
| | |
|---|---|
| *G05D 1/00* | (2024.01) |
| *A61L 9/01* | (2006.01) |
| *G01S 17/931* | (2020.01) |

(52) U.S. Cl.
CPC .............. *G05D 1/0251* (2013.01); *A61L 9/01* (2013.01); *G01S 17/931* (2020.01);
(Continued)

(58) Field of Classification Search
CPC .... G05D 1/0251; G05D 1/0214; G05D 1/242; G05D 1/246; G05D 1/617; G05D 2105/10; G05D 2109/10; G05D 2111/17; G05D 1/2435; A61L 9/01; A61L 2209/111; A61L 2209/14; G01S 17/931; A47L 11/4011; A47L 11/4097; A47L 2201/04; A47L 2201/06; B25J 11/00; B25J 5/007; B25J 9/0009; B25J 9/1664; B25J 9/1697;
(Continued)

(56) References Cited

U.S. PATENT DOCUMENTS

2019/0079531 A1*   3/2019   Haegermarck ..... A47L 11/4061

FOREIGN PATENT DOCUMENTS

| | | | | |
|---|---|---|---|---|
| CN | 111258225 A | * | 6/2020 | ............. G05B 15/02 |
| EP | 3695694 A1 | * | 8/2020 | ........... A01B 69/008 |

(Continued)

OTHER PUBLICATIONS

English translation of KR-2366330-B1 (Year: 2025).*
(Continued)

*Primary Examiner* — Scott A Browne
*Assistant Examiner* — Shahira Baajour
(74) *Attorney, Agent, or Firm* — Ladas & Parry, LLP

(57) ABSTRACT

Disclosed herein is a disinfection robot. The disinfection robot includes a body provided with an outlet, a fan provided inside the body, a fan motor configured to rotate the fan, a wheel provided under the body, a wheel motor configured to rotate the wheel, a three-dimensional camera having a forward field of view of the body and configured to capture a three-dimensional image, and a processor configured to control the fan motor to rotate the fan to discharge air through the outlet and control the wheel motor to rotate the wheel to move the body based on the three-dimensional image.

10 Claims, 9 Drawing Sheets

(52) U.S. Cl.
CPC ....... *G05D 1/0214* (2013.01); *A61L 2209/111*
(2013.01); *A61L 2209/14* (2013.01)

(58) Field of Classification Search
CPC ... B25J 13/08; B25J 19/02; F24F 8/10; G01N
21/94
See application file for complete search history.

(56) References Cited

FOREIGN PATENT DOCUMENTS

| | | | |
|---|---|---|---|
| KR | 10-1659037 | B | 9/2016 |
| KR | 10-2019-0027974 | A | 3/2019 |
| KR | 10-2020-0102108 | A | 8/2020 |
| KR | 10-2021-0005986 | A | 1/2021 |
| KR | 10-2021-0069847 | A | 6/2021 |
| KR | 10-2296693 | B | 8/2021 |
| KR | 10-2021-0122962 | A | 10/2021 |
| KR | 2366330 | B1 * | 2/2022 |
| TW | I733105 | B | 7/2021 |

OTHER PUBLICATIONS

English Translation of CN-111258225-A (Year: 2025).*
Extended European Search Report from European Patent Application No. 23200858.1 dated Feb. 21, 2024.
Office action from South Korean Patent Application No. 2022-0125838 dated Dec. 4, 2023.
Notice of Allowance from South Korean Patent Application No. 2022-0125838 dated Jan. 23, 2024.

* cited by examiner

DISINFECTION ROBOT AND CONTROLLING METHOD THEREOF

CROSS-REFERENCE TO RELATED APPLICATION

This application claims the benefit of Korean Patent Application No. 10-2022-0125838, filed on Sep. 30, 2022 in the Korean Intellectual Property Office, the disclosure of which is incorporated herein by reference.

BACKGROUND

1. Field

Embodiments of the present disclosure relate to a movable disinfection robot and a method of controlling the same.

2. Description of the Related Art

A disinfection device is a device for suctioning indoor air, disinfecting the suctioned air, and discharging the disinfected air. In this case, disinfection refers to appropriately controlling the cleanliness of indoor air or the like.

The disinfection device may control the cleanliness of the indoor air by removing pollutants in the air. The disinfection device may remove bacteria, viruses, mold, fine dust, and chemicals that cause bad odors present in the suctioned air.

The disinfection device may be equipped with a filter for purifying polluted indoor air. The air suctioned into the disinfection device may be purified to be clean air by removing pollutants while passing through the filter, and the purified air may be discharged to the outside of the disinfection device.

For the purifying operation of the disinfection device, it is necessary to measure a pollution level of a disinfection space. In order to measure the pollution level of the disinfection space, the disinfection device may include a particle sensor for irradiating a laser beam to fine particles contained in the air and then measuring the pollution level through an amount of the beam scattered by the particles.

The disinfection device may not be moved, and thus may not actively respond to a change according to pollutants in the air.

SUMMARY

Therefore, it is an aspect of the present disclosure to provide a movable disinfection robot and a method of controlling the same.

It is another aspect of the present disclosure to provide a disinfection robot, which may detect and avoid a stepped portion and/or a ramp while moving, and a method of controlling the same.

Additional aspects of the disclosure will be set forth in part in the description which follows and, in part, will be obvious from the description, or may be learned by practice of the disclosure.

In accordance with one aspect of the present disclosure, a disinfection robot includes a body provided with an outlet, a fan provided inside the body, a fan motor configured to rotate the fan, a wheel provided under the body, a wheel motor configured to rotate the wheel, a three-dimensional camera having a forward field of view of the body and configured to capture a three-dimensional image, and a processor configured to control the fan motor to rotate the fan to discharge air through the outlet and control the wheel motor to rotate the wheel to move the body based on the three-dimensional image.

The processor may identify a change in height of a floor in front of the body based on the three-dimensional image, and control the wheel motor to avoid a zone in which the change in height is larger than a first reference value based on the change in height larger than the first reference value.

The processor may identify a change in slope of a floor in front of the body based on the three-dimensional image, and control the wheel motor to avoid a zone in which the change in slope is larger than a second reference value based on the change in slope larger than the second reference value.

The processor may divide the three-dimensional image into a plurality of buckets, acquire an average distance of the plurality of buckets, and identify a change in height of adjacent buckets based on a difference between average distances to the adjacent buckets.

The processor may control the wheel motor to avoid a zone in which the change in height is larger than a first reference value.

The processor may identify a slope between the adjacent buckets based on an angle formed by the change in height of the adjacent buckets, and identify a slope difference between the adjacent buckets based on the difference between the slopes between the adjacent buckets.

The processor may control the wheel motor to avoid a zone in which a change in slope is larger than a second reference value.

The processor may include geographical map data corresponding to an air purification space including a plurality of zones and air quality map data indicating air quality of the plurality of zones, and control the wheel motor to move the body based on the geographical map data and the air quality map data.

In accordance with another aspect of the present disclosure, a method of controlling a disinfection robot including a body provided with an outlet, a fan provided inside the body, and a wheel provided under the body includes capturing a three-dimensional image through a three-dimensional camera having a forward field of view of the body, rotating the fan to discharge air through the outlet, and rotating the wheel to move the body based on the three-dimensional image.

In accordance with still another aspect of the present disclosure, a disinfection robot includes a body provided with an outlet, a fan provided inside the body, a fan motor configured to rotate the fan, a wheel provided under the body, a wheel motor configured to rotate the wheel, a light detection and ranging (LiDAR) sensor configured to acquire LiDAR data with a forward field of sensing of the body, and a processor configured to control the fan motor to rotate the fan to discharge air through the outlet and control the wheel motor to rotate the wheel to move the body based on the LiDAR data.

In accordance with yet another aspect of the present disclosure, a method of controlling a disinfection robot including a body provided with an outlet, a fan provided inside the body, and a wheel provided under the body includes acquiring LiDAR data through a LiDAR sensor having a forward field of sensing of the body, rotating the fan to discharge air through the outlet, and rotating the wheel to move the body based on the LiDAR data.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

The same reference numbers may denote the same components throughout the specification.

The specification does not describe all elements of embodiments, and general contents or overlapping contents between the embodiments in the technical field to which the present disclosure pertains will be omitted.

Terms "unit," "module," "member," and "block" used in the specification may be implemented as software or hardware, and according to the embodiments, a plurality of "units, modules, members, and blocks" may be implemented as one component, or one "unit, module, member, and block" may also include a plurality of components.

Throughout the specification, when a first component is described as being "connected" to a second component, this includes not only a case in which the first component is directly connected to the second component but also a case in which the first component is indirectly connected to the second component, and the indirect connection includes connection through a wireless communication network.

Throughout the specification, when the first component is described as "including" the second component, this means further including the third component rather than precluding the third component unless especially stated otherwise.

Throughout the specification, when a first member is described as being positioned "on" a second member, this includes both a case in which the first member is in contact with the second member and a case in which a third member is present between the two members. In addition, terms used throughout the specification, such as "front," "rear," "left," and "right" are defined based on the drawings, and a shape and a position of each component are not limited by the terms.

Throughout the specification, terms such as first and second are used to distinguish a first component from a second component, and the components are not limited by the above-described terms.

Throughout the specification, the singular expression includes the plural expression unless the context clearly dictates otherwise.

In each operation, identification symbols are used for convenience of description, and the identification symbols do not describe the sequence of each operation, and each operation may be performed in a different sequence from the specified sequence unless a specific sequence is clearly described in context.

Hereinafter, an operation principle and embodiments of the present disclosure will be described with reference to the accompanying drawings.

Figure 1:
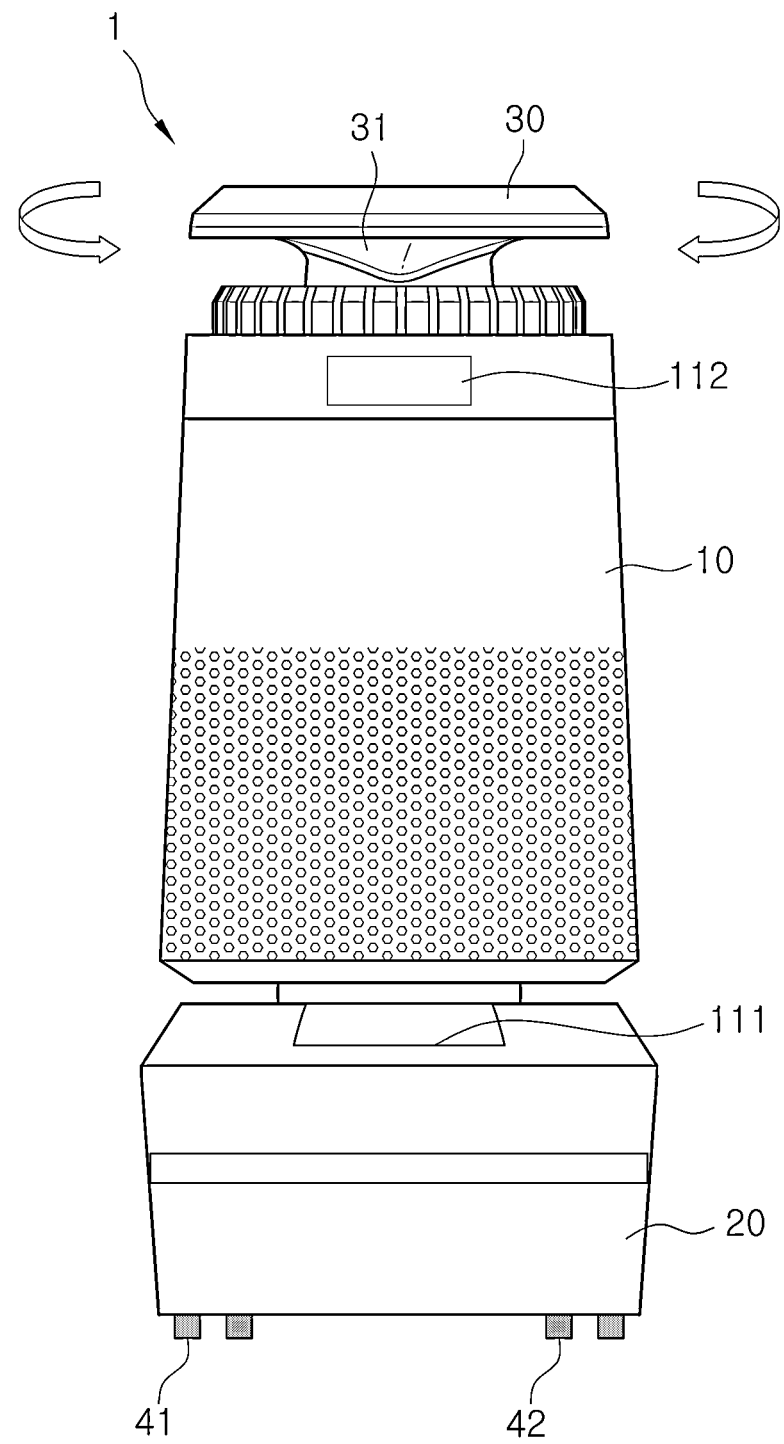
FIG. 1 is a view illustrating an exterior of a disinfection robot according to one embodiment.

FIG. 1 is a view illustrating an exterior of a disinfection robot according to one embodiment.

Referring to FIG. 1, a disinfection robot 1 may include a disinfection body 10 provided in a substantially cylindrical shape, and a moving body 20 provided under the disinfection body 10. However, the shapes of the disinfection body 10 and the moving body 20 are not limited to a cylinder and may be provided in various shapes such as a polyhedron. In addition, the disinfection body 10 and the moving body 20 may be provided separately or integrally. Components for purifying air in a disinfection space may be provided in the disinfection body 10 of the disinfection robot 1. For example, the disinfection body 10 may include a fan 50 for suctioning air in the disinfection space, a filter for purifying the suctioned air, and the like.

A cover 30 may be formed above the disinfection body 10.

The cover 30 may be provided to be rotated with respect to the disinfection body 10. As illustrated in FIG. 1, the cover 30 may rotate clockwise or counterclockwise with respect to the disinfection body 10.

An outlet 31 through which the air purified by the filter is discharged may be provided on the cover 30. The outlet 31 may discharge the air purified by the filter in a specific direction.

The outlet 31 may be rotated according to the rotation of the cover 30. For example, when the cover 30 rotates clockwise with respect to the disinfection body 10, the outlet 31 may also rotate clockwise with respect to the disinfection body 10, and a discharged direction of the air purified by the filter may also be rotated clockwise. In addition, when the cover 30 rotates counterclockwise with respect to the disinfection body 10, the outlet 31 may also rotate counterclockwise with respect to the disinfection body 10, and a discharged direction of the air purified by the filter may also be rotated counterclockwise.

Components for moving the disinfection robot 1 may be provided in the moving body 20. For example, the moving body 20 may include a first wheel 41 and a second wheel 42 for moving the disinfection robot 1.

The first wheel 41 and the second wheel 42 may be provided on a lower surface of the moving body 20 and may rotate so that the disinfection robot 1 may move. For example, the first wheel 41 may be provided on a left end of the lower surface of the moving body 20, and the second wheel 42 may be provided on a right end of the lower surface of the moving body 20. The moving body 20 may be moved in a forward, rearward, leftward, or rightward direction by the rotation of the first wheel 41 and the second wheel 42.

Figure 2:
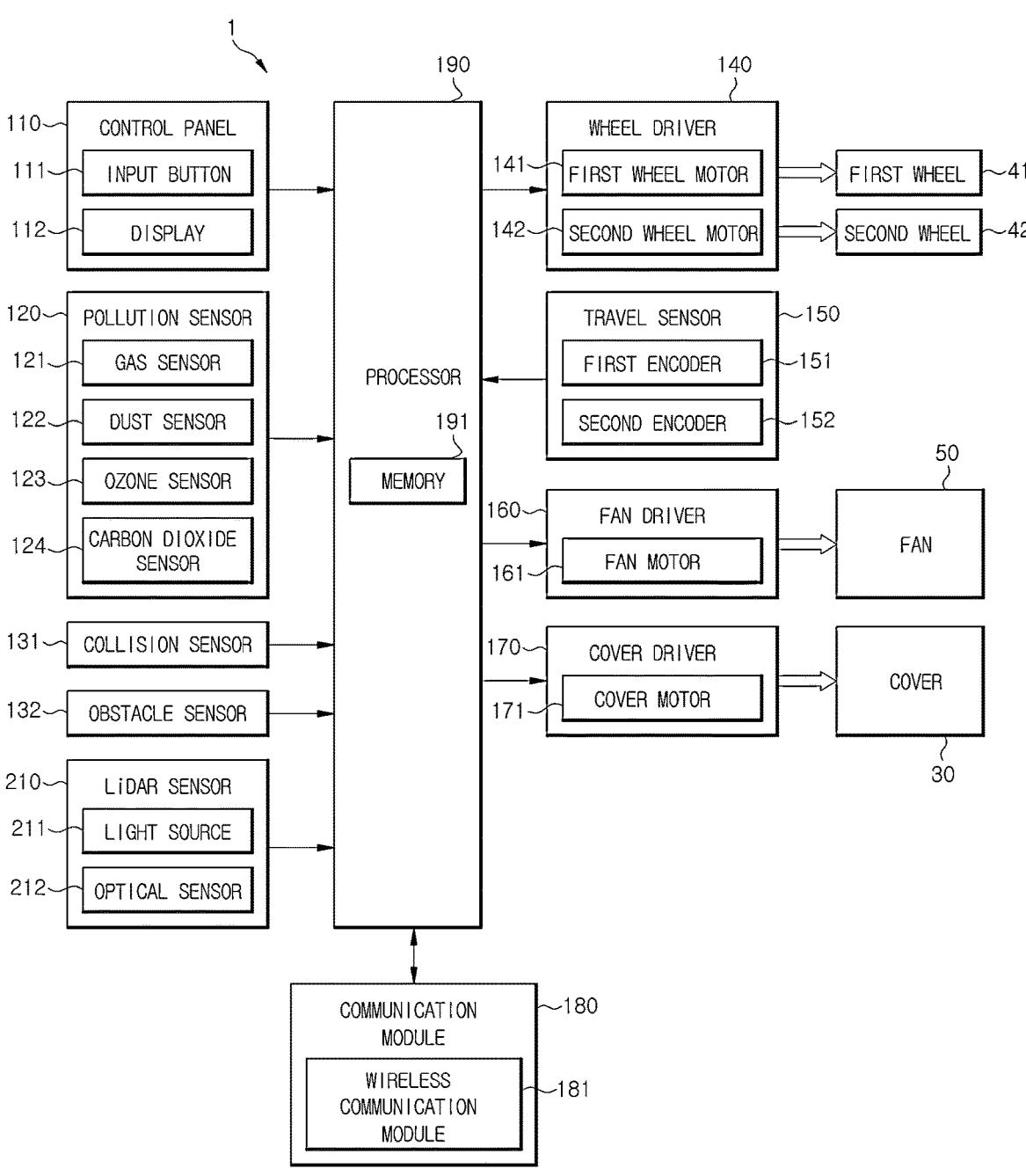
FIG. 2 is a view illustrating a configuration of the disinfection robot according to one embodiment.
Figure 3A:
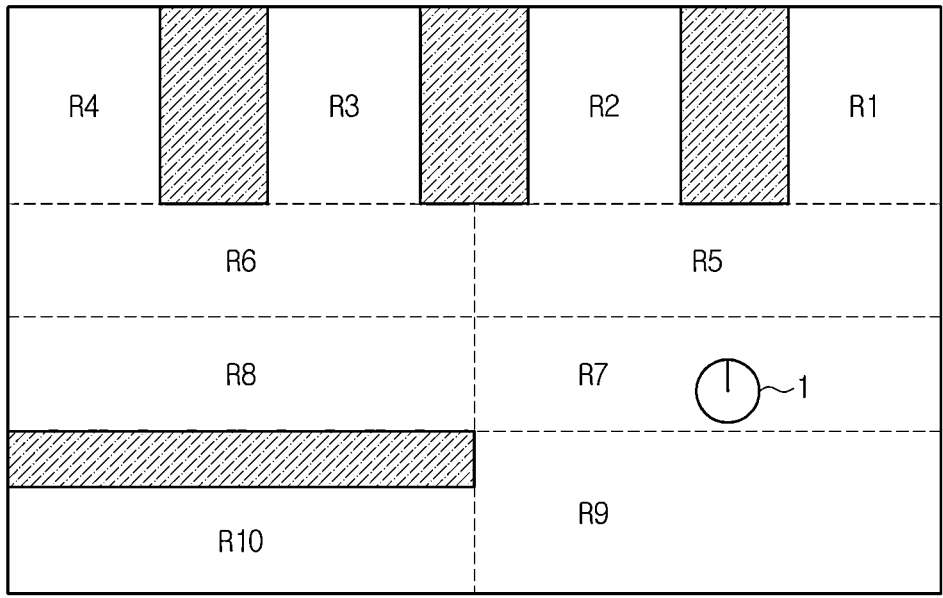
FIGS. 3A and 3B are a view illustrating geographical map data and air quality map data of the disinfection robot according to one embodiment.
Figure 3B:
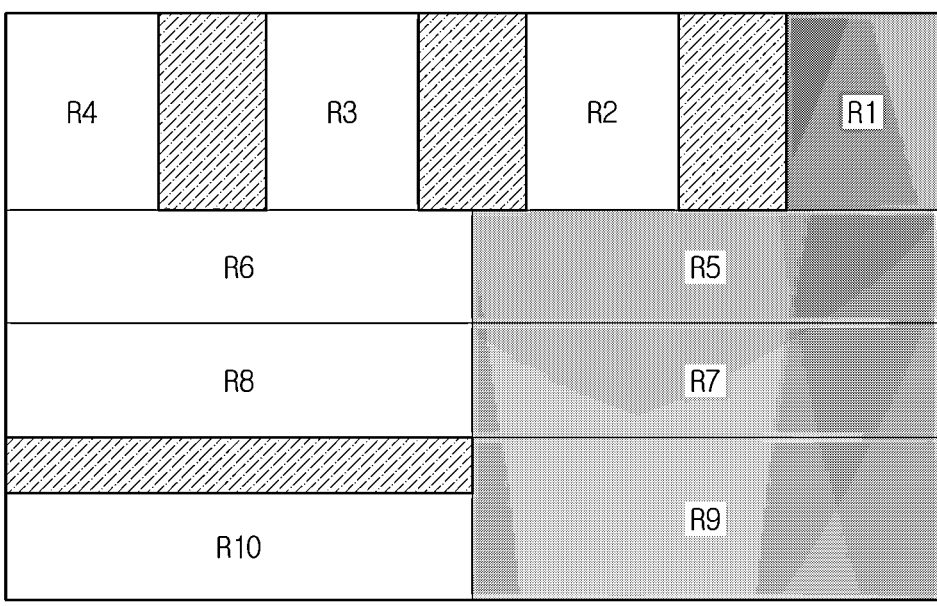
Figure 4:
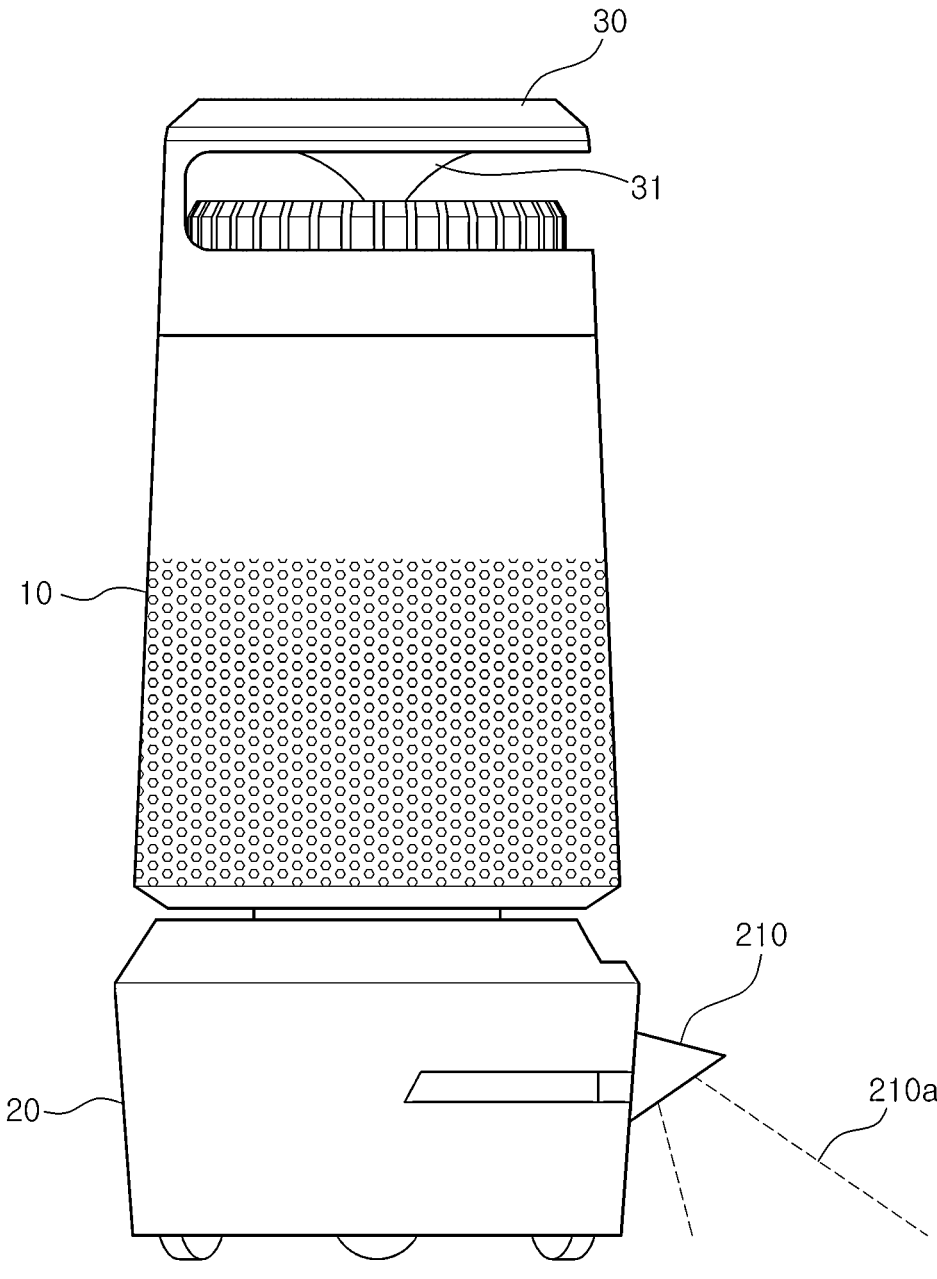
FIG. 4 is a view illustrating an example of a light detection and ranging (LiDAR) sensor included in the disinfection robot according to one embodiment.

FIG. 2 is a view illustrating a configuration of the disinfection robot according to one embodiment. FIGS. 3A and 3B are a view illustrating geographical map data and air quality map data of the disinfection robot according to one embodiment. FIG. 4 is a view illustrating an example of a light detection and ranging (LiDAR) sensor included in the disinfection robot according to one embodiment.

Referring to FIGS. 2, 3, and 4, the disinfection robot 1 may include a control panel 110, a pollution sensor 120, a collision sensor 131, an obstacle sensor 132, a wheel driver 140, a travel sensor 150, a fan driver 160, a cover driver 170, a communication module 180, a LiDAR sensor 210, and/or a processor 190. The control panel 110, the pollution sensor 120, the collision sensor 131, the obstacle sensor 132, the wheel driver 140, the travel sensor 150, the fan driver 160, the cover driver 170, the communication module 180, the LiDAR sensor 210, and/or the processor 190 do not correspond to essential components of the disinfection robot 1, and at least some of the components may be omitted.

The control panel 110 may provide a user with a user interface for interaction with the user.

The control panel 110 may include an input button 111 or a display 112.

The input button 111 may acquire a user's input related to an operation of the disinfection robot 1. For example, the input button 111 may acquire a flow amount or rate of the air discharged by the disinfection robot 1.

The input button 111 may include a tact switch, a push switch, a slide switch, a toggle switch, a micro switch, or a touch switch.

The display 112 may display operation information of the disinfection robot 1. In addition, the display 112 may display the user's input acquired in relation to the operation of the disinfection robot 1. For example, the display 112 may display the flow amount or rate of the air discharged by the disinfection robot 1.

The display 112 may include, for example, a liquid crystal display (LCD) panel, a light emitting diode (LED) panel, and the like.

The pollution sensor 120 may collect information about pollutants contained in the air in the disinfection space. For example, the pollution sensor 120 may collect information about a concentration of an odor-causing particle (hereinafter referred to as "gas") contained in the air and/or information about a concentration of dust.

The pollution sensor 120 may include a gas sensor 121, a dust sensor 122, an ozone sensor 123, and/or a carbon dioxide sensor 124. The gas sensor 121, the dust sensor 122, the ozone sensor 123, and/or the carbon dioxide sensor 124 do not correspond to essential components, and at least some of the components may be omitted.

The gas sensor 121 may measure a concentrations of a gas contained in the air and output an electrical signal indicating the concentration of the gas. For example, the gas sensor 121 may detect the gas in the air or measure the concentration of the gas in the air using a change in electrical conductivity of a semiconductor device occurring when the ozone is collected on a surface of the semiconductor.

The processor 190 may identify the concentration of the ozone contained in the air in the disinfection space based on an output of the gas sensor 121.

The dust sensor 122 may measure a concentration of dust contained in the air and output an electrical signal indicating the concentrations of the dust. For example, the dust sensor 122 may detect the dust in the air or measure the concentration of the dust in the air using the scattering of light by the dust contained in the air.

The processor 190 may identify the concentration of the dust contained in the air in the disinfection space based on an output of the dust sensor 122.

The ozone sensor 123 may measure a concentration of ozone contained in the air and output an electrical signal indicating the concentration of the ozone. For example, the ozone sensor 123 may detect the ozone in the air or measure the concentration of the ozone in the air using a change in electrical conductivity of a semiconductor device occurring when the ozone is collected on the surface of the semiconductor.

The processor 190 may identify the concentration of the ozone contained in the air in the disinfection space based on an output of the ozone sensor 123.

The carbon dioxide sensor 124 may measure a concentration of carbon dioxide contained in the air and output an electrical signal indicating the concentration of the carbon dioxide. For example, the carbon dioxide sensor 124 may detect the carbon dioxide in the air or measure the concentration of the carbon dioxide in the air using the absorption of infrared rays by the carbon dioxide contained in the air.

The processor 190 may identify the concentration of the carbon dioxide contained in the air in the disinfection space based on an output of the carbon dioxide sensor 124.

The collision sensor 131 may be positioned inside a bumper of the moving body 20 and may identify a collision with an obstacle.

The bumper may be provided on a front surface of the moving body 20 and may reduce an impact transmitted to the moving body 20 in the event of the collision with the obstacle. The bumper may transmit the impact caused by the collision in the event of the collision with the obstacle to a collision switch.

For example, the collision sensor 131 may include the collision switch. The collision switch may detect a collision between the bumper and the obstacle. The opened (turned off) collision switch may be closed (turned on) by the collision between the bumper and the obstacle. When the bumper collides with the obstacle, the collision switch may provide the processor 190 with a collision detection signal (e.g., a voltage signal or a current signal) indicating the collision with the obstacle.

The obstacle sensor 132 may be positioned inside the moving body 20. The obstacle sensor 132 may identify the presence or absence of the obstacle and/or a distance to the obstacle without contact or collision with the obstacle.

The obstacle sensor 132 may transmit infrared rays, ultrasonic waves, or radio waves forward from the moving body 20 and receive infrared rays, ultrasonic waves, or radio waves reflected from the obstacle. The obstacle sensor 132 may identify the presence or absence of the obstacle and/or the distance to the obstacle based on the received infrared rays, ultrasonic waves, or radio waves.

For example, the obstacle sensor 132 may include a photo diode for emitting infrared rays and a photo sensor. The photo diode may emit the infrared rays forward from the disinfection robot 1, and the photo sensor may receive the infrared rays reflected from the obstacle positioned in front of the disinfection robot 1. The obstacle sensor 132 may identify the presence or absence of the obstacle and/or the distance to the obstacle based on an intensity of the infrared ray received by the photo sensor.

The wheel driver 140 may move the moving body 20 in response to a control signal of the processor 190.

The wheel driver 140 may include a first wheel motor 141 and a second wheel motor 142. The first wheel motor 141 may rotate the first wheel 41, and the second wheel motor 142 may rotate the second wheel 42. The first wheel motor 141 and the second wheel motor 142 may independently rotate the first wheel 41 and the second wheel 42 by the control signal of the processor 190. The first wheel 41 may be rotated by the first wheel motor 141 independently of the rotation of the second wheel 42, and the second wheel 42 may be rotated by the second wheel motor 142 independently of the rotation of the first wheel 41.

The wheel driver 140 may further include a driving circuit for supplying a driving current to each of the first wheel motor 141 and the second wheel motor 142 in response to the control signal of the processor 190, a power transmission device for transmitting the rotation of the first and second wheel motors 141 and 142 to the first and second wheels 41 and 42, respectively, and the like.

The travel sensor 150 may be installed on each of the first wheel 41 and the second wheel 42 and may detect rotation speeds and rotation directions of the first wheel 41 and the second wheel 42.

The travel sensor 150 includes a first encoder 151 and a second encoder 152.

The first encoder 151 may detect the rotation speed and the rotation direction of the first wheel 41, and the second encoder 152 may detect the rotation speed and the rotation direction of the second wheel 42.

For example, the first encoder 151 and the second encoder 152 may each include a disk in which a plurality of slits are formed, a light emitting diode for emitting light, and a photo diode for detecting light passing through the plurality of slits. The first encoder 151 and the second encoder 152 may respectively identify the rotation speeds and the rotation directions of the first wheel 41 and the second wheel 42 based on a detection cycle and the number of detections for the light detected by the photo diode.

In addition, the first encoder 151 and the second encoder 152 may each include a disk on which a plurality of permanent magnets are installed and a Hall sensor for detecting magnetic fields generated by the plurality of permanent magnets. The first encoder 151 and the second encoder 152 may identify the rotation speeds and the rotation directions of the first wheel 41 and the second wheel 42, respectively, based on a detection cycle and the number of detections for the magnetic field detected by the Hall sensor.

The first encoder 151 and the second encoder 152 my each provide the processor 190 with information about the rotation speed and the rotation direction of the first wheel 41 and information about the rotation speed and the rotation direction of the second wheel 42.

The fan driver 160 may drive the fan 50 included in the disinfection body 10 in response to a control signal of the processor 190.

The fan driver 160 may include a fan motor 161. The fan motor 161 may rotate the fan 50. By the rotation of the fan 50, air outside the disinfection robot 1 may be suctioned into the disinfection robot 1. The suctioned air may be forcibly moved to the filter by the rotation of the fan 50. While the suctioned air passes through the filter, foreign substances or the like contained in the suctioned air may be filtered by the filter.

The fan driver 160 may further include a driving circuit for supplying a driving current to the fan motor 161 in response to the control signal of the processor 190, a power transmission device for transmitting the rotation of the fan motor 161 to the fan 50, and the like.

The cover driver 170 may rotate the cover 30 in response to a control signal of the processor 190.

The cover driver 170 may include a cover motor 171. The cover motor 171 may be connected to a rotational shaft of the cover 30 and may rotate the cover 30 clockwise or counterclockwise with respect to the disinfection body 10. By the rotation of the cover 30, a direction in which the outlet 31 faces may be changed, and a direction in which the air passing through the filter is discharged may also be changed.

The cover driver 170 may further include a driving circuit for supplying a driving current to the cover motor 171 in response to the control signal of the processor 190, a power transmission device for transmitting the rotation of the cover motor 171 to the cover 30, and the like.

The communication module 180 may include a communication circuit capable of transmitting or receiving data to or from a user device (e.g., a portable device) and/or a communication circuit capable of transmitting or receiving data to or from a service device (e.g., a server device).

The communication module 180 may include a wireless communication module 181 capable of wirelessly transmitting or receiving data to or from the user device and/or the service device.

For example, the wireless communication module 181 may wirelessly communicate with a base station or an access point (AP) and may be connected to a wired communication network through the base station or the AP. The wireless communication module 181 may communicate with the user device and/or the service device connected to the wired communication network via the base station or the AP. For example, the wireless communication module 181 may wirelessly communicates with the AP using WiFi™ (IEEE 802.11 technical standard) or communicate with the base station using code division multiple access (CDMA), wideband CDMA (WCDMA), a global system for mobiles (GSM), long term evolution (LTE), wireless broadband Internet (WiBro), or the like. The wireless communication module 181 may also transmit or receive data to or from the user device via the service device through the wired communication network.

In addition, the wireless communication module 181 may wirelessly communicate with the user device directly. For example, the wireless communication module 181 may wirelessly transmit or receive data to or from the user device using WiFi Direct, Bluetooth™ (IEEE 802.15.1 technical standard), ZigBee™ (IEEE 802.15.4 technical standard), or the like.

The LiDAR sensor 210 may transmit light (e.g., infrared rays) toward an area around the disinfection robot 1 and detect an obstacle and/or a stepped portion to the disinfection robot 1 based on the reflected light reflected from the obstacle and/or the stepped portion. For example, as illustrated in FIG. 4, the LiDAR sensor 210 may be installed on the moving body 20 of the disinfection robot 1 and may have a field of view 210*a* facing the floor in front of the disinfection robot 1.

The LiDAR sensor 210 may include a light source 211 (e.g., a light emitting diode, a light emitting diode array, a laser diode, or a laser diode array) for emitting light (e.g., infrared rays), and an optical sensor 212 (e.g., a photo diode or a photo diode array) for receiving light (e.g., infrared rays). In addition, as necessary, the LiDAR sensor 210 may further include a driving device for rotating the light source and/or the optical sensor.

The LiDAR sensor 210 may emit light through the light source 211 and receive light reflected from the floor, the obstacle, or the stepped portion through the optical sensor, and thus acquire LiDAR data. The LiDAR data may include a relative position (distance to a nearby object and/or direction of the nearby object) and/or a relative speed of a nearby obstacle and/or stepped portion to the disinfection robot 1.

The LiDAR sensor 210 may provide the LiDAR data to the processor 190.

The processor 190 may be electrically connected to the control panel 110, the pollution sensor 120, the collision sensor 131, the obstacle sensor 132, the wheel driver 140, the travel sensor 150, the fan driver 160, the cover driver 170, the communication module 180, and/or the LiDAR sensor 210.

The processor 190 may acquire information about the surroundings of the disinfection robot 1 from the sensor and generate the control signal for controlling the operation of the disinfection robot 1 based on the acquired information.

The processor 190 may process electrical signals or data received from the control panel 110, the pollution sensor 120, the collision sensor 131, the obstacle sensor 132, the travel sensor 150, and/or the LiDAR sensor 210 and acquire related environmental information. For example, the processor 190 may acquire information about the user's input from the control panel 110. The processor 190 may acquire information about a collision with an obstacle from the collision sensor 131. The processor 190 may acquire information about the presence or absence of the obstacle and a distance to the obstacle from the obstacle sensor 132. The processor 190 may receive information about the rotation speeds and the rotation directions of the first and second wheels 41 and 42 from the travel sensor 150. The processor 190 may acquire the LiDAR data including information about the stepped portion and/or the ramp from the LiDAR sensor 210.

The processor 190 may provide the control signal or control data to the wheel driver 140, the fan driver 160, and the cover driver 170 based on a result of processing the acquired information. For example, the processor 190 may control the first and second wheel motors 141 and 142 to rotate the first and second wheels 41 and 42 based on the information about the stepped portion and/or the ramp. For example, the processor 190 may control the first and second wheel motors 141 and 142 to rotate the first and second wheels 41 and 42 based on the information (collision, presence, or distance) about the obstacle. The processor 190 may control the fan motor 161 to rotate the fan 50 based on the information about the user's input. The processor 190 may control the cover motor 171 to rotate the cover 30 based on the information about the user's input.

The processor 190 may receive a reception signal from the communication module 180 and also provide a transmission signal to the communication module 180.

The processor 190 may include a memory 191 for recording and/or storing a program and data for generating the control signal.

The memory 191 may temporarily remember electrical signals or data received from the control panel 110, the pollution sensor 120, the collision sensor 131, the obstacle sensor 132, and the travel sensor 150 and remember temporary data generated while processing the received electrical signals or data. In addition, the memory 191 may temporarily remember the control signal or the control data to be provided to the wheel driver 140, the fan driver 160, and the cover driver 170.

The memory 191 may include not only volatile memories such as a static random access memory (SRAM) and a dynamic RAM (DRAM) but also non-volatile memories such as a flash memory, a read only memory (ROM), and an erasable programmable ROM (EPROM).

The memory 191 may be provided integrally with the processor 190 or provided separately from the processor 190.

As described above, the processor 190 may control the components included in the disinfection robot 1 so that the disinfection robot 1 may travel in the disinfection space and purify the air in the disinfection space.

The processor 190 may store geographical map data of the disinfection space in the memory 191 so that the disinfection robot 1 efficiently travels in the disinfection space.

For example, the geographical map data of the disinfection space may be stored in advance or generated based on a travel record recorded while the disinfection robot 1 travels in the disinfection space.

For example, the processor 190 may acquire the information (e.g., the information about the rotation speeds and/or the rotation directions) about the rotations of the first and second wheels 41 and 42 from the travel sensor 150 while the disinfection robot 1 travels and determine a moving vector indicating a moving speed and a moving direction of the disinfection robot 1 based on the information about the rotations of the first and second wheels 41 and 42.

The processor 190 may determine a current position (relative position from a reference point) of the disinfection robot 1 based on a position of the reference point and the moving vector of the disinfection robot 1. The processor 190 may store the travel record including current positions of the disinfection robot 1 acquired every predetermined time. In addition, the processor 190 may generate the geographical map data of the disinfection space based on the travel record and control the disinfection robot 1 to efficiently travel in the disinfection space.

The geographical map data may include information about zones in which the disinfection robot 1 may travel. A disinfection space of the geographical map data may be divided into a plurality of zones according to the arrangement of obstacles and the like that the disinfection robot 1 may not travel. For example, as illustrated in FIG. 3A, the geographical map data may be partitioned into a first zone R1, a second zone R2, a third zone R3, a fourth zone R4, a fifth zone R5, a sixth zone R6, a seventh zone R7, an eighth zone R8, a ninth zone R9, and a tenth zone R10 according to the arrangement of the obstacles and the like.

The processor 190 may store air quality map data of the disinfection space in the memory 191 in order to efficiently purify the air in the disinfection space.

For example, the air quality map data of the disinfection space may be stored in advance or generated based on air quality records recorded while the disinfection robot 1 travels in the disinfection space.

The processor 190 may store the travel record including the current positions of the disinfection robot 1 while the disinfection robot 1 travels in the disinfection space. In this case, the processor 190 may acquire an air pollution level corresponding to the current position based on the output of the pollution sensor 120. The air pollution level may indicate a degree of pollution of the air and may be calculated based on the gas concentration, the dust concentration, the ozone concentration, and/or the carbon dioxide concentration. When the air pollution level is high, this may indicate that the gas concentration, the dust concentration, the ozone concentration, and/or the carbon dioxide concentration in the air are high and the air quality is low, and when the air pollution level is low, this may mean that the gas concentration, the dust concentration, the ozone concentration, and/or the carbon dioxide concentration in the air are low and the air quality is high.

The processor 190 may generate the air quality map data corresponding to the geographical map data based on the air pollution level corresponding to the current position.

As described above, the disinfection space of the geographical map data may be divided into the plurality of zones. The air quality map data may include the air pollution level corresponding to each of the plurality of zones. For example, as illustrated in FIG. 3B, the air quality map data may include an air pollution level of the first zone R1, an air pollution level of the second zone R2, an air pollution level of the third zone R3, an air pollution level of the fourth zone R4, an air pollution level of the fifth zone R5, an air pollution level of the sixth zone R6, an air pollution level of the seventh zone R7, an air pollution level of the eighth zone R8, an air pollution level of the ninth zone R9, and an air pollution level of the tenth zone R10.

The processor 190 may control the disinfection robot 1 to travel in the disinfection space in order to efficiently purify the air in the disinfection space based on the geographical map data and the air quality map data.

The disinfection robot 1 may determine the pollution level on the floor of the disinfection space and sterilize the floor of the disinfection space using an ultraviolet light source (UV light emitting diode (LED)). For example, the processor 190 may identify the pollution level on the floor of the disinfection space using an infrared sensor or the like while the disinfection robot 1 travels in the disinfection space and generate pollution level map data of the floor based on the identified pollution level of the floor. The processor 190 may generate a travel route for sterilizing the floor based on the pollution level map data of the floor and control the wheel driver 140 so that the disinfection robot 1 travels along the generated travel route. In addition, the processor 190 may sterilize the floor of the disinfection space while the disinfection robot 1 travels in the disinfection space. Specifically, the processor 190 may control the UV LED to irradiate ultraviolet rays toward the floor of the disinfection space.

A specific method of the disinfection robot 1 efficiently traveling in the disinfection space will be described in detail below.

Figure 5:
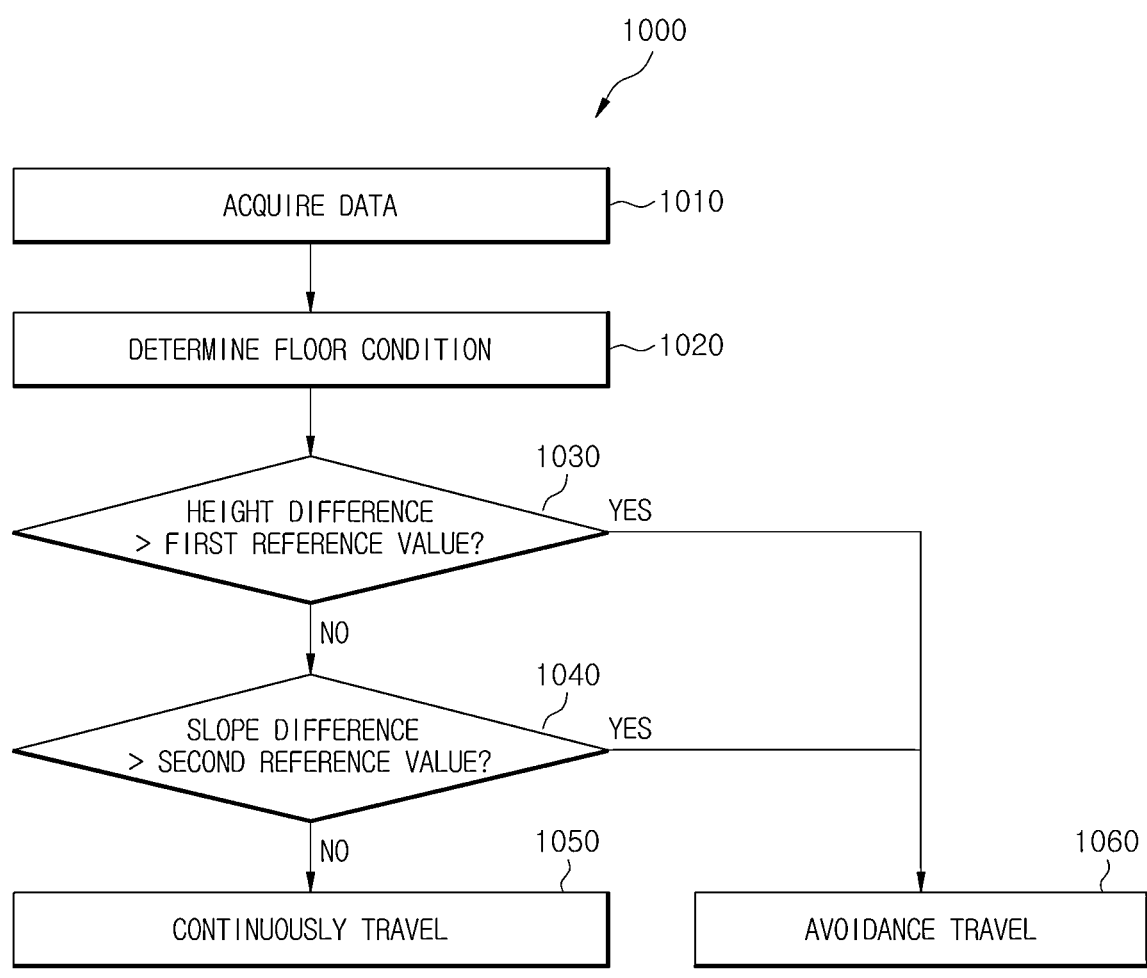
FIG. 5 is a view illustrating a method of the disinfection robot according to one embodiment identifying a stepped portion and/or a ramp on a floor.

FIG. 5 is a view illustrating a method of the disinfection robot according to one embodiment identifying a stepped portion and/or a ramp on a floor.

A method 1000 in which the disinfection robot 1 identifies the stepped portion and/or the ramp will be described with reference to FIG. 5.

The disinfection robot 1 may acquire floor data of the disinfection space (1010).

The processor 190 may control the LiDAR sensor 210 to acquire information about the floor while the disinfection robot 1 travels in the disinfection space.

The LiDAR sensor 210 may control the light source 211 to emit light toward the floor on which the disinfection robot 1 travels and acquire light reflected from the floor through the optical sensor 212. The LiDAR sensor 210 may provide LiDAR data including floor height information to the processor 190 based on the reflected light.

The processor 190 may acquire the LiDAR data including the floor height information from the LiDAR sensor 210.

The disinfection robot 1 may determine a floor condition (1020).

The processor 190 may process the LiDAR data acquired from the LiDAR sensor 210 and identify a change (e.g., the stepped portion and/or the ramp) in height of the floor. For example, the processor 190 may identify the change in height of the floor and/or a change in slope of the floor.

The disinfection robot 1 may determine whether the change in height of the floor is larger than a first reference value (1030).

The processor 190 may identify the change in height of the floor based on a difference between a previously acquired height of the floor and a currently acquired height of the floor.

The processor 190 may compare the change in height of the floor to the first reference value and identify whether the change in height of the floor is larger than the first reference value. Here, the first reference value may be set experimentally or empirically and for example, set based on the stepped portion that the disinfection robot 1 may not pass thereover. For example, the first reference value may be a value between 3 and 7 cm, and preferably, may be about 5 cm.

When the change in height of the floor is not larger than the first reference value (NO in 1030), the disinfection robot 1 may determine whether the change in slope of the floor is larger than a second reference value (1040).

The processor 190 may calculate a moving distance of the disinfection robot 1 between sampling cycles of the LiDAR sensor 210 based on the sampling cycle of the LiDAR sensor 210 and the moving speed of the disinfection robot 1. The processor 190 may identify the slope of the floor based on the moving distance of the disinfection robot 1 between the sampling periods of the LiDAR sensor 210 and the change in height of the floor. In addition, the processor 190 may identify a change in slope of the floor based on a difference between a previously acquired slope of the floor and a currently acquired slope of the floor.

The processor 190 may compare the change in slope of the floor to the second reference value and identify whether the change in slope of the floor is larger than the second reference value. Here, the second reference value may be set experimentally or empirically and for example, set based on the change in slope that the disinfection robot 1 may not pass thereover. For example, the second reference value may be a value between 10 and 20 degrees and preferably, may be about 15 degrees.

When the change in slope of the floor is not larger than the second reference value (NO in 1040), the disinfection robot 1 may continuously travel (1050).

When the change in height of the floor is not larger than the first reference value and the change in slope of the floor is not larger than the second reference value, the processor 190 may control the disinfection robot to continuously travel along a current travel route.

When the change in height of the floor is larger than the first reference value (YES in 1030) or the change in slope of the floor is larger than the second reference value (YES in 1040), the disinfection robot 1 may avoid the stepped portion or the ramp on the floor (1060).

When the change in height of the floor is larger than the first reference value, the processor 190 may control the rotations of the first and second wheels 41 and 42 so that the disinfection robot 1 travels along an outline of the stepped portion (e.g., a position at which the change in height of the floor is larger than the first reference value) on the floor.

In addition, when the change in slope of the floor is larger than the second reference value, the processor 190 may control the rotations of the first and second wheels 41 and 42 so that the disinfection robot 1 travels along an outline of the ramp (e.g., a position at which the change in slope of the floor is larger than the second reference value) on the floor.

As described above, the disinfection robot 1 may identify the stepped portion and/or the ramp on the floor using the LiDAR sensor 210. The disinfection robot 1 may avoid the stepped portion and/or the ramp in response to the identification of the stepped portion and/or the ramp on the floor.

Therefore, it is possible to suppress, minimize, or prevent the restriction to the movement of the disinfection robot 1 due to the stepped portion and/or the ramp on the floor.

Figure 6:
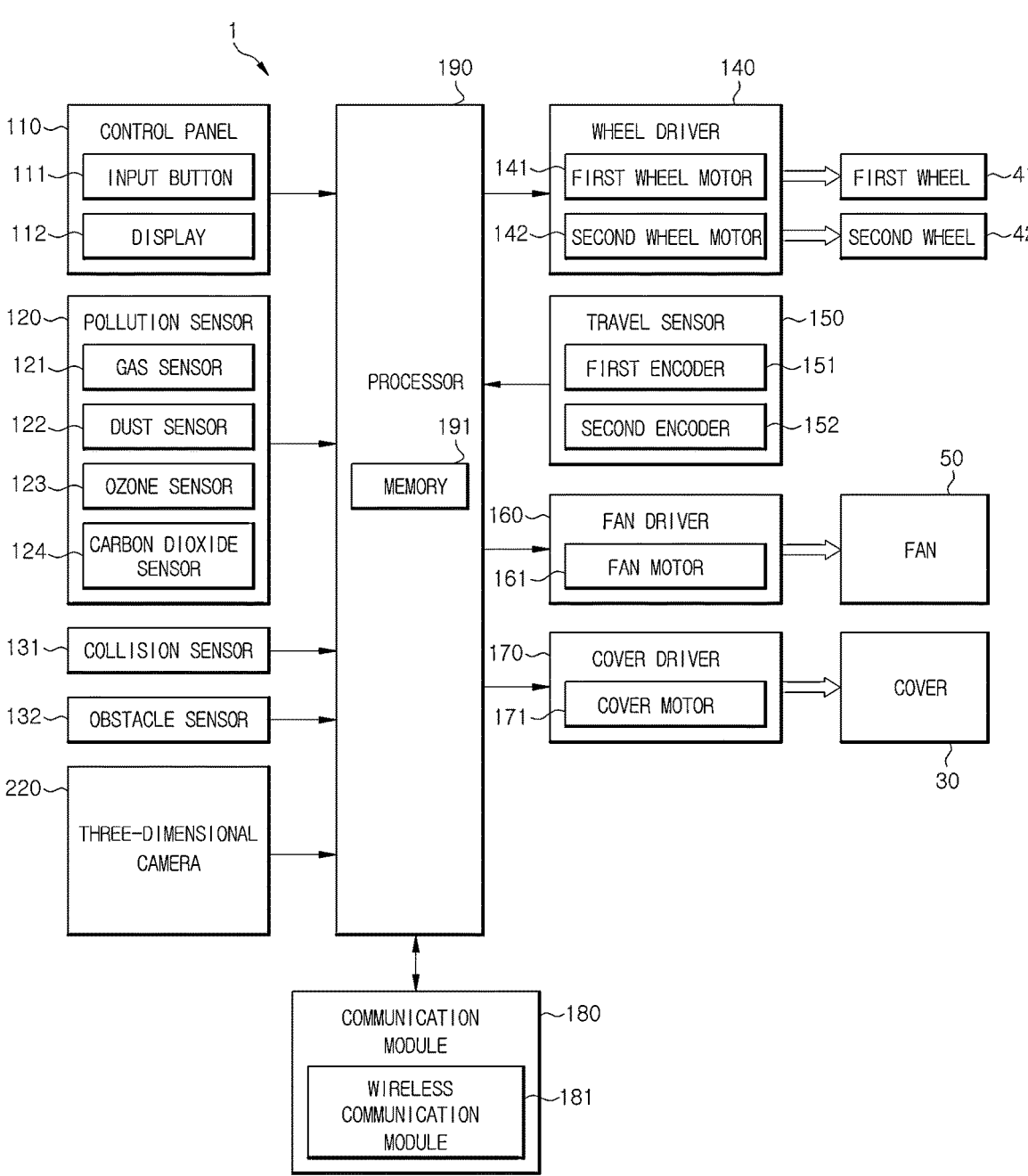
FIG. 6 is a view illustrating a configuration of the disinfection robot according to one embodiment.
Figure 7:
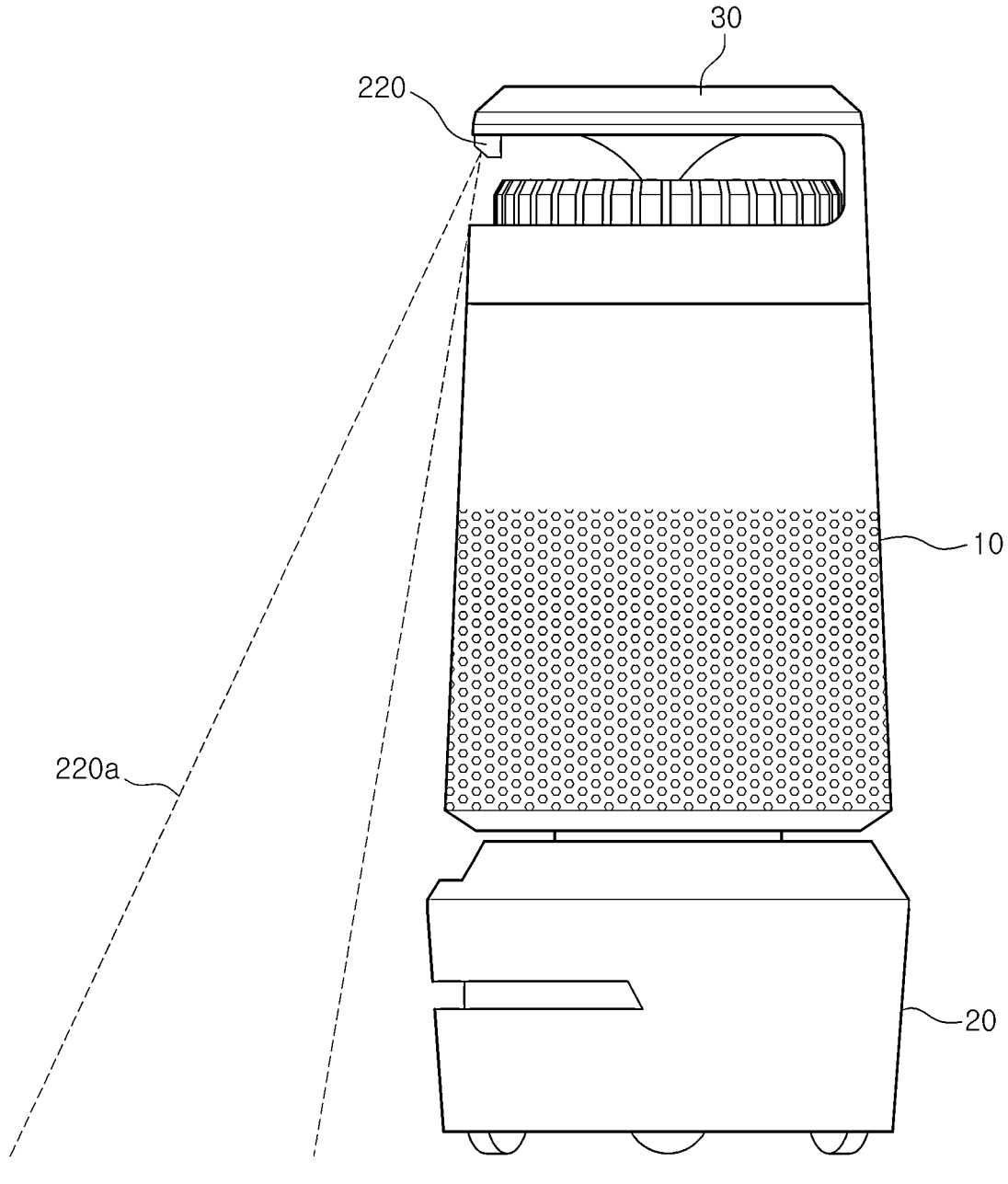
FIG. 7 is a view illustrating an example of a three-dimensional camera included in the disinfection robot according to one embodiment.

FIG. 6 is a view illustrating a configuration of the disinfection robot according to one embodiment. FIG. 7 is a view illustrating an example of a three-dimensional camera included in the disinfection robot according to one embodiment.

Referring to FIGS. 6 and 7, the disinfection robot 1 may include a control panel 110, a pollution sensor 120, a collision sensor 131, an obstacle sensor 132, a wheel driver 140, a travel sensor 150, a fan driver 160, a cover driver 170, a communication module 180, a three-dimensional camera 220, and/or a processor 190. The control panel 110, the pollution sensor 120, the collision sensor 131, the obstacle sensor 132, the wheel driver 140, the travel sensor 150, the fan driver 160, the cover driver 170, the communication module 180, the three-dimensional camera 220, and/or the processor 190 do not correspond to essential components of the disinfection robot 1, and at least some of the components may be omitted.

The control panel 110, the pollution sensor 120, the collision sensor 131, the obstacle sensor 132, the wheel driver 140, the travel sensor 150, the fan driver 160, the cover driver 170, the communication module 180, and/or the processor 190 may be the same as the control panel 110, the pollution sensor 120, the collision sensor 131, the obstacle sensor 132, the wheel driver 140, the travel sensor 150, the fan driver 160, the cover driver 170, the communication module 180, and/or the processor 190 illustrated in FIG. 2.

The three-dimensional camera 220 may acquire three-dimensional images around the disinfection robot 1. The three-dimensional image may include a two-dimensional image including a plurality of pixels arranged in a matrix form and distance information of each of the plurality of pixels forming the two-dimensional image. In other words, the three-dimensional image may include the two-dimensional image and the distance information of each pixel.

For example, as illustrated in FIG. 7, the three-dimensional camera 220 may be provided on the cover 30 of the disinfection robot 1 and may have a field of view 220a facing the floor in front of the disinfection robot 1.

In order to acquire the three-dimensional image including the distance information of each pixel, the three-dimensional camera 220 may include a pair of cameras (e.g., stereo cameras) spaced apart from each other or include a camera and a distant sensor (e.g., an infrared sensor or an ultrasonic sensor).

When the three-dimensional camera 220 includes the pair of cameras, the three-dimensional camera 220 may identify a distance to a captured object based on a difference between a pair of images captured by the pair of cameras. In addition, when the three-dimensional camera 220 includes the distant sensor, the three-dimensional camera 220 may identify the distance to the captured object based on the output of the distant sensor.

The three-dimensional camera 220 may provide the processor 190 with the three-dimensional image including the distance information and the two-dimensional image.

The processor 190 may process the three-dimensional image received from the three-dimensional camera 220 and acquire related environmental information. The processor 190 may process the three-dimensional image and acquire the information about the stepped portion and/or the ramp in the disinfection space.

Hereinafter, a specific method of the disinfection robot 1 efficiently traveling in the disinfection space will be described in detail below.

Figure 8:
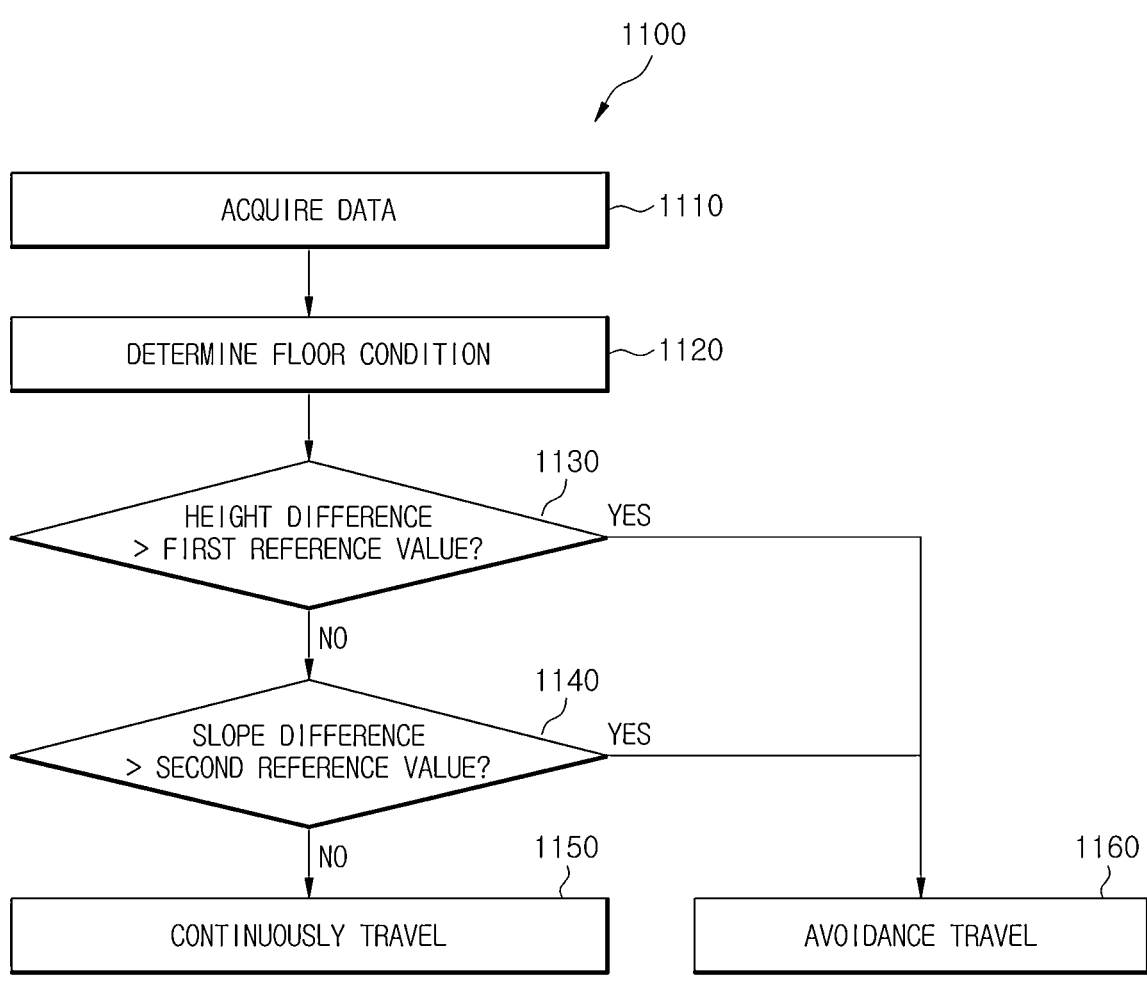
FIG. 8 is a view illustrating a method of the disinfection robot according to one embodiment identifying a stepped portion and/or a ramp on a floor.
Figure 9:
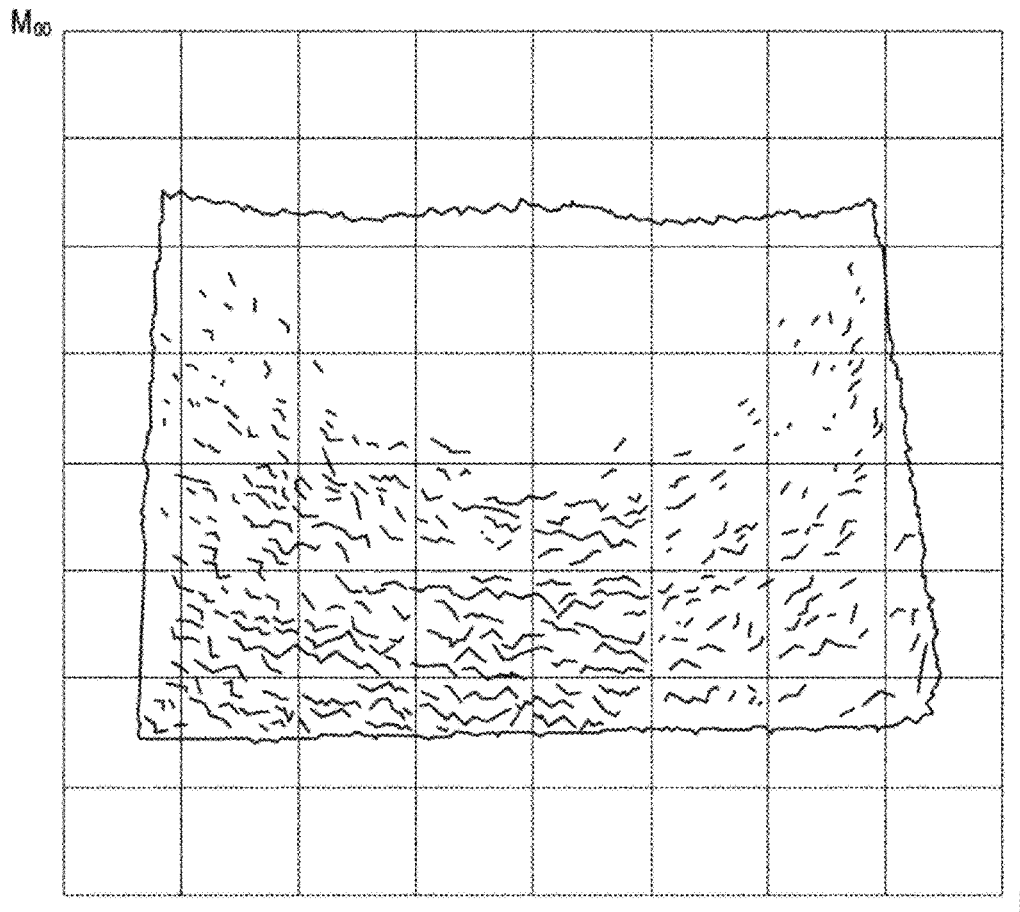
FIG. 9 is a view illustrating an example in which the disinfection robot according to one embodiment processes a three-dimensional image.

FIG. 8 is a view illustrating a method of the disinfection robot according to one embodiment identifying a stepped portion and/or a ramp on a floor. FIG. 9 is a view illustrating an example in which the disinfection robot according to one embodiment processes a three-dimensional image.

A method 1100 in which the disinfection robot 1 identifies the stepped portion and/or the ramp on the floor will be described with reference to FIGS. 8 and 9.

The disinfection robot 1 may acquire three-dimensional image data of the floor of the disinfection space (1010).

The processor 190 may control the three-dimensional camera 220 to acquire information about the floor while the disinfection robot 1 travels in the disinfection space.

The three-dimensional camera 220 may acquire the three-dimensional image of the floor on which the disinfection robot 1 travels and provide the processor 190 with the three-dimensional image.

For example, as illustrated in FIG. 8, the processor 190 may acquire the three-dimensional image including information on the height of the floor.

The disinfection robot 1 may determine a floor condition (1020).

The processor 190 may process the three-dimensional image and identify a change (e.g., the stepped portion and/or the ramp) in height of the floor. For example, the processor 190 may identify the change in height of the floor and/or a change in slope of the floor.

The processor 190 may classify a plurality of pixels of the three-dimensional image into a plurality of buckets. For example, the processor 190 may acquire a three-dimensional image including 640*480 pixels and divide the three-dimensional image into 20*20 buckets.

The processor 190 may calculate an average distance to each bucket. For example, the processor 190 may calculate the average distance to each bucket using Equation 1.

$$M_{ij} = \frac{1}{n}\sum\nolimits_{k=0}^{n} P_k \qquad \text{[Equation 1]}$$

Here, $M_{ij}$ denotes an average distance to buckets in an $i^{th}$ row and a $j^{th}$ column, and $p_k$ denotes distances between pixels within the bucket.

The processor 190 may identify a change in height based on the average distance to each bucket. Specifically, the processor 190 may identify a change in height of the floor based on a difference between the average distances to adjacent buckets. For example, the processor 190 may identify the change in height using Equation 2.

$$H_{left,i,j} = Z_{i+1,j+1} - Z_{i,j}$$

$$H_{right,i,j} = Z_{i-1,j+1} - Z_{i,j}$$

$$H_{front,i,j} = Z_{i,j+1} - Z_{i,j} \qquad \text{[Equation 2]}$$

Here, $Z_{i,j}$ denotes a distance (height) in the $i^{th}$ row and the $j^{th}$ column, $Z_{i+1,j+1}$ denotes a distance (height) of an $(i+1)^{th}$ row and a $(j+1)^{th}$ column, and $H_{left,i,j}$ denotes a height difference at a front left side of the $i^{th}$ row and the $j^{th}$ column.

$Z_{i-1,j+1}$ denotes a distance (height) of an $(i-1)^{th}$ row and the $(j+1)^{th}$ column, and $H_{right,i,j}$ denotes a height difference at a front right side of the $i^{th}$ row and the $j^{th}$ column.

In addition, $Z_{i,j+1}$ denotes a distance (height) of the $i^{th}$ row and the $(j+1)^{th}$ column, and $H_{front,ij}$ denotes a height difference at the front of the $i^{th}$ row and the $j^{th}$ column.

The processor 190 may identify the slope based on a change in height of the adjacent buckets. Specifically, the processor 190 may identify the slope between the adjacent buckets based on an angle formed by the change in height of the adjacent buckets. For example, the processor 190 may identify the slope using Equation 3.

$$\Theta_{left,i,j}=\mathrm{angle}(H_{left,i,j+1}, H_{left,i,j})$$

$$\Theta_{right,i,j}=\mathrm{angle}(H_{right,i,j+1}, H_{right,i,j})$$

$$\Theta_{front,i,j}=\mathrm{angle}(H_{front,i,j+1}, H_{front,i,j}) \quad \text{[Equation 3]}$$

Here, $H_{left,i,j+1}$ denotes a height difference at a front left side of the $i^{th}$ row and the $(j+1)^{th}$ column, $H_{left,i,j}$ denotes a height difference of the front left side of the $i^{th}$ row and the $j^{th}$ column, and $\Theta_{left,i,j}$ denotes a slope at the front left side of the $i^{th}$ row and the $j^{th}$ column.

$H_{right,i,j+1}$ denotes a height difference of a front right side of the $i^{th}$ row and the $(j+1)^{th}$ column, $H_{right,i,j}$ denotes a height difference of a front right side of the $i^{th}$ row and the $j^{th}$ column, and $\Theta_{right,i,j}$ denotes a slope at the front right side of the $i^{th}$ row and the $j^{th}$ column.

In addition, $H_{front,i,j+1}$ denotes a height difference at the front of the $i^{th}$ row and the $(j+1)^{th}$ column, $H_{front,i,j}$ denotes a height difference at the front of the $i^{th}$ row and the $j^{th}$ column, and $\Theta_{front,i,j}$ denotes a slope at the front of the $i^{th}$ row and the $j^{th}$ column.

The processor 190 may identify the change in slope based on slope information of each bucket. Specifically, the processor 190 may identify the change in slope based on the difference between the adjacent buckets. For example, the processor 190 may identify the change in slope using Equation 4.

$$\omega_{left,i,j}=\Theta_{left,i,j+1}-\Theta_{left,i,j}$$

$$\omega_{right,i,j}=\Theta_{right,i,j+1}-\Theta_{right,i,j}$$

$$\omega_{front,i,j}=\Theta_{front,i,j+1}-\Theta_{front,i,j} \quad \text{[Equation 4]}$$

Here, $\Theta_{left, i,j+1}$ denotes a slope at the front left of the $i^{th}$ row and the $(j+1)^{th}$ column, $\Theta_{left,i,j}$ denotes a slope at the front left side of the $i^{th}$ row and the $j^{th}$ column, and $\omega_{left,i,j}$ denotes a slope difference at the front left side of the $i^{th}$ row and the $j^{th}$ column.

$\Theta_{right,i,j+1}$ denotes a slope at the front right side of the $i^{th}$ row and the $(j+1)^{th}$ column, $\Theta_{right,i,j}$ denotes a slope at the front right side of the $i^{th}$ row and the $j^{th}$ column, and $\omega_{right,i,j}$ denotes a slope difference at the front right side of the $i^{th}$ row and the $j^{th}$ column.

In addition, $\Theta_{front,i,j+1}$ denotes a slope at the front of the $i^{th}$ row and the $(j+1)^{th}$ column, $\Theta_{front,i,j}$ denotes a slope at the front of the $i^{th}$ row and the $j^{th}$ column, and $\omega_{front,i,j}$ denotes a slope difference at the front of the $i^{th}$ row and the $j^{th}$ column.

As described above, the processor 190 may process the three-dimensional image and calculate the height difference and/or slope difference of the floor in front of the disinfection robot 1.

The disinfection robot 1 may determine whether the change in height of the floor is larger than a first reference value (1130).

The processor 190 may identify the change in height of the floor based on a difference between a previously acquired height of the floor and a currently acquired height of the floor. For example, the processor 190 may identify the change in height of the floor using Equation 2.

The processor 190 may compare the change in height of the floor to the first reference value and identify whether the change in height of the floor is larger than the first reference value. Here, the first reference value may be set experimentally or empirically and for example, set based on the stepped portion that the disinfection robot 1 may not pass thereover. For example, the first reference value may be a value between 3 and 7 cm, and preferably, may be about 5 cm.

When the change in height of the floor is not larger than the first reference value (NO in 1130), the disinfection robot 1 may determine whether a change in slope of the floor is larger than a second reference value (1140).

The processor 190 may identify the change in slope of the floor based on a difference between a previously acquired slope of the floor and a currently acquired slope of the floor. For example, the processor 190 may identify the change in slope of the floor using Equation 4.

The processor 190 may compare the change in slope of the floor to the second reference value and identify whether the change in slope of the floor is larger than the second reference value. Here, the second reference value may be set experimentally or empirically and for example, set based on the change in slope that the disinfection robot 1 may not pass thereover. For example, the second reference value may be a value between 10 and 20 degrees and preferably, may be about 15 degrees.

When the change in slope of the floor is not larger than the second reference value (NO in 1140), the disinfection robot 1 may continuously travel (1150). When the change in height of the floor is larger than the first reference value (YES in 1130) or the change in slope of the floor is larger than the second reference value (YES in 1140), the disinfection robot 1 may avoid the stepped portion or the ramp on the floor (1160).

The operations 1150 and 1160 may be the same as the operations 1050 and 1060 illustrated in FIG. 5.

As described above, the disinfection robot 1 may identify the stepped portion and/or the ramp on the floor using the three-dimensional camera 220. The disinfection robot 1 may avoid the stepped portion and/or the ramp in response to the identification of the stepped portion and/or the ramp on the floor. Therefore, it is possible to suppress, minimize, or prevent the restriction to the movement of the disinfection robot 1 due to the stepped portion and/or the ramp on the floor.

Meanwhile, disclosed embodiments may be implemented in the form of a recording medium in which commands executable by a computer are stored. The commands may be stored in the form of program code, and when executed by a processor, program modules are generated to perform operations of the disclosed embodiments. The recording medium may be implemented as a computer-readable recording medium.

The computer-readable recording medium includes any type of recording media in which commands that may be decoded by a computer are stored. For example, there may be a ROM, a RAM, a magnetic tape, a magnetic disk, a flash memory, an optical data storage device, and the like.

A device-readable storage medium may be provided in the form of a non-transitory storage medium. Here, "non-transitory" is a tangible device and only means not including a signal (e.g., electromagnetic waves), and this term does not distinguish between cases in which data is stored semi-permanently and temporarily in the storage medium. For example, "non-temporary storage medium" may include a buffer in which data is temporarily stored.

As is apparent from the above description, it is possible to provide a movable disinfection robot and a method of controlling the same.

According to one aspect of the present disclosure, it is possible to provide the disinfection robot which may detect and avoid a stepped portion and/or a ramp while moving, and the method of controlling the same.

As described above, the disclosed embodiments have been described with reference to the accompanying drawings. Those skilled in the art to which the present disclosure pertains will understand that the present disclosure can be carried out in the form different from the disclosed embodiments without changing the technical spirit or essential features of the present disclosure. The disclosed embodiments are illustrative and should not be construed as being limited.

What is claimed is:

1. A disinfection robot comprising:
a body provided with an outlet;
a fan provided inside the body;
a fan motor configured to rotate the fan;
a wheel provided under the body;
a wheel motor configured to rotate the wheel;
a three-dimensional camera having a forward field of view of the body and configured to capture a three-dimensional image; and
a processor configured to control the fan motor to rotate the fan to discharge air through the outlet and control the wheel motor to rotate the wheel to move the body based on the three-dimensional image,
wherein the processor is configured to: identify a change in slope of a floor in front of the body based on the three-dimensional image; and control the wheel motor to travel along an outline of a zone in which the change in slope is larger than a slope change reference value based on the change in slope larger than the slope change reference value;
wherein the processor is configured to: identify a change in height of the floor in front of the body based on the three-dimensional image; and control the wheel motor to avoid a zone in which the change in height is larger than a height change reference value based on the change in height larger than the height change reference value,
wherein the processor is configured to: divide the three-dimensional image into a plurality of buckets; acquire an average distance to each of the plurality of buckets; identify a change in height of adjacent buckets among the plurality of buckets based on a difference between average distances to the adjacent buckets; and identify the change in height of the floor in front of the body based on the change in height of the adjacent buckets.

2. The disinfection robot of claim 1, wherein the processor is configured to control the wheel motor to avoid a zone in which the change in height is larger than the height change reference value.

3. The disinfection robot of claim 1, wherein the processor is configured to: identify a slope between the adjacent buckets based on an angle formed by the change in height of the adjacent buckets; and identify a slope difference between the adjacent buckets based on the difference between the slopes between the adjacent buckets.

4. The disinfection robot of claim 1, wherein the processor includes geographical map data corresponding to an air purification space including a plurality of zones and air quality map data indicating air quality of the plurality of zones, and the processor is configured to control the wheel motor to move the body based on the geographical map data and the air quality map data.

5. A method of controlling a disinfection robot including a body provided with an outlet, a fan provided inside the body, and a wheel provided under the body, the method comprising: capturing a three-dimensional image through a three-dimensional camera having a forward field of view of the body; rotating the fan to discharge air through the outlet; and rotating the wheel to move the body based on the three-dimensional image, and
wherein the rotating of the wheel to move the body based on the three-dimensional image includes:
identifying a change in slope of a floor in front of the body based on the three-dimensional image; and
controlling the wheel motor to travel along an outline of a zone in which the change in slope is larger than a slope change reference value based on the change in slope larger than the slope change reference value;
wherein the rotating of the wheel to move the body based on the three- dimensional image includes: identifying a change in height of the floor in front of the body based on the three-dimensional image; and rotating the wheel to avoid a zone in which the change in height is larger than a height change reference value based on the change in height larger than the height change reference value,
wherein the rotating of the wheel to move the body based on the three- dimensional image includes: dividing the three-dimensional image into a plurality of buckets; acquiring an average distance to each of the plurality of buckets; identifying a change in height of adjacent buckets among the plurality of buckets based on a difference between average distances to the adjacent buckets; and identifying the change in height of the floor in front of the body based on the change in height of the adjacent buckets.

6. The method of claim 5, wherein the rotating of the wheel to move the body based on the three-dimensional image further includes rotating the wheel to avoid a zone in which the change in height is larger than the height change reference value.

7. The method of claim 5, wherein the rotating of the wheel to move the body based on the three-dimensional image includes: identifying a slope between the adjacent buckets based on an angle formed by the change in height of the adjacent buckets; and identifying a slope difference between the adjacent buckets based on the difference between the slopes between the adjacent buckets.

8. The method of claim 5, further comprising rotating the wheel to move the body based on geographical map data corresponding to a disinfection purification space and including a plurality of zones and air quality map data indicating air quality of the plurality of zones.

9. A disinfection robot comprising: a body provided with an outlet; a fan provided inside the body; a fan motor configured to rotate the fan; a wheel provided under the body; a wheel motor configured to rotate the wheel; a light detection and ranging (LiDAR) sensor configured to acquire LiDAR data with a forward field of sensing of the body; and a processor configured to control the fan motor to rotate the fan to discharge air through the outlet and control the wheel motor to rotate the wheel to move the body based on the LiDAR data, wherein the processor is configured to identify a change in slope of a floor corresponding to a ramp in front of the body based on the LiDAR data; and control the wheel motor to:

travel along an outline of a zone in which the change in slope is larger than a slope change reference value based on the change in slope being larger than the slope change reference value; and continuously travel a zone in which the detected change in slope is not larger than the slope change reference value.

10. The disinfection robot of claim 9, wherein the processor is configured to: identify a change in height of the floor in front of the body based on the LiDAR data; and control the wheel motor to avoid a zone in which the change in height is larger than a first reference value based on the change in height larger than the first reference value.

\* \* \* \* \*